United States Patent
Erbs

(10) Patent No.: US 8,226,954 B2
(45) Date of Patent: Jul. 24, 2012

(54) POLYPEPTIDE HAVING AN IMPROVED CYTOSINE DEAMINASE ACTIVITY

(75) Inventor: Philippe Erbs, Strasbourg (FR)

(73) Assignee: Transgene S.A., Illkirch (FR)

( * ) Notice: Subject to any disclaimer, the term of this patent is extended or adjusted under 35 U.S.C. 154(b) by 32 days.

(21) Appl. No.: 12/822,314

(22) Filed: Jun. 24, 2010

(65) Prior Publication Data

US 2010/0330031 A1 Dec. 30, 2010

Related U.S. Application Data

(62) Division of application No. 10/565,230, filed as application No. PCT/IB2004/002505 on Jun. 29, 2004, now Pat. No. 7,790,445.

(60) Provisional application No. 60/508,274, filed on Oct. 6, 2003.

(30) Foreign Application Priority Data

Jul. 21, 2003 (EP) .................................. 03360087

(51) Int. Cl.
*A61K 39/00* (2006.01)
*C12P 21/04* (2006.01)
*C07K 1/00* (2006.01)
*C07H 21/04* (2006.01)

(52) U.S. Cl. .................... 424/192.1; 435/69.7; 530/350; 530/371; 536/23.4

(58) Field of Classification Search ............... 424/192.1; 435/69.7; 530/350, 371; 536/23.4
See application file for complete search history.

(56) References Cited

U.S. PATENT DOCUMENTS

| 5,545,548 | A  | 8/1996 | Senter et al. |
| 6,552,005 | B1 | 4/2003 | Buchsbaum et al. |
| 7,572,438 | B2 | 8/2009 | Erbs et al. |

FOREIGN PATENT DOCUMENTS

| WO | WO 94/28143 A1   | 12/1994 |
| WO | WO 99/54481 A1   | 10/1999 |
| WO | WO 2004/061079 A2 | 7/2004 |

OTHER PUBLICATIONS

Miyagi et al., Gene therapy for prostate cancer using the cytosine deaminase/uracil phosphoribosyltransferase suicide system the Journal of Gene Medicine vol. 5, Issue 1, pp. 30-37, Jan. 2003.*

Ngo, in The Protein Folding Problem and Tertiary Structure Prediction, Merz et al. (eds.), Birkhauser Boston: Boston, MA, pp. 433 and 492-495, 1994.*

Erbs et al. "In Vivo Cancer Gene Therapy by Adenovirus-mediated Transfer of a Bifunctional Yeast Cytosine Deaminase/Uracil Phosphoribosyltransferase Fusion Gene", Cancer Research, Jul. 2000, pp. 3813-3822, vol. 60.

Kern et al., "The *FUR1* gene of *Saccharomyces cerevisiae*: cloning, structure and expression of wild-type and mutant alleles", Gene., 1990, pp. 149-157, vol. 88, No. 2.

Meyer et al., "Mapping of deletions in the genome of the highly attenuated vaccinia virus MVA and their influence on virulence", Journal of General Virology, 1991, pp. 1031-1038, vol. 72.

Wybranietz et al., "Enhanced suicide gene effect by adenoviral transduction of a VP22-cytosine deaminase (CD) fusion gene", Gene Therapy, 2001, pp. 1654-1664, vol. 8.

Chung-Faye et al., "In vivo gene therapy for colon cancer using adenovirus-mediated, transfer of the fusion gene cytosine deaminase and uracil phosphoribosyltransferase", Gene Therapy, 2001, pp. 1547-1557, vol. 8.

* cited by examiner

*Primary Examiner* — Maria Leavitt
(74) *Attorney, Agent, or Firm* — Buchanan Ingersoll & Rooney PC

(57) ABSTRACT

The present invention relates to a polypeptide possessing a CDase activity, characterized in that it is derived from a native CDase by addition of an amino acid sequence with the proviso that said polypeptide has no UPRtase or Thymidine Kinase activity.

4 Claims, 1 Drawing Sheet

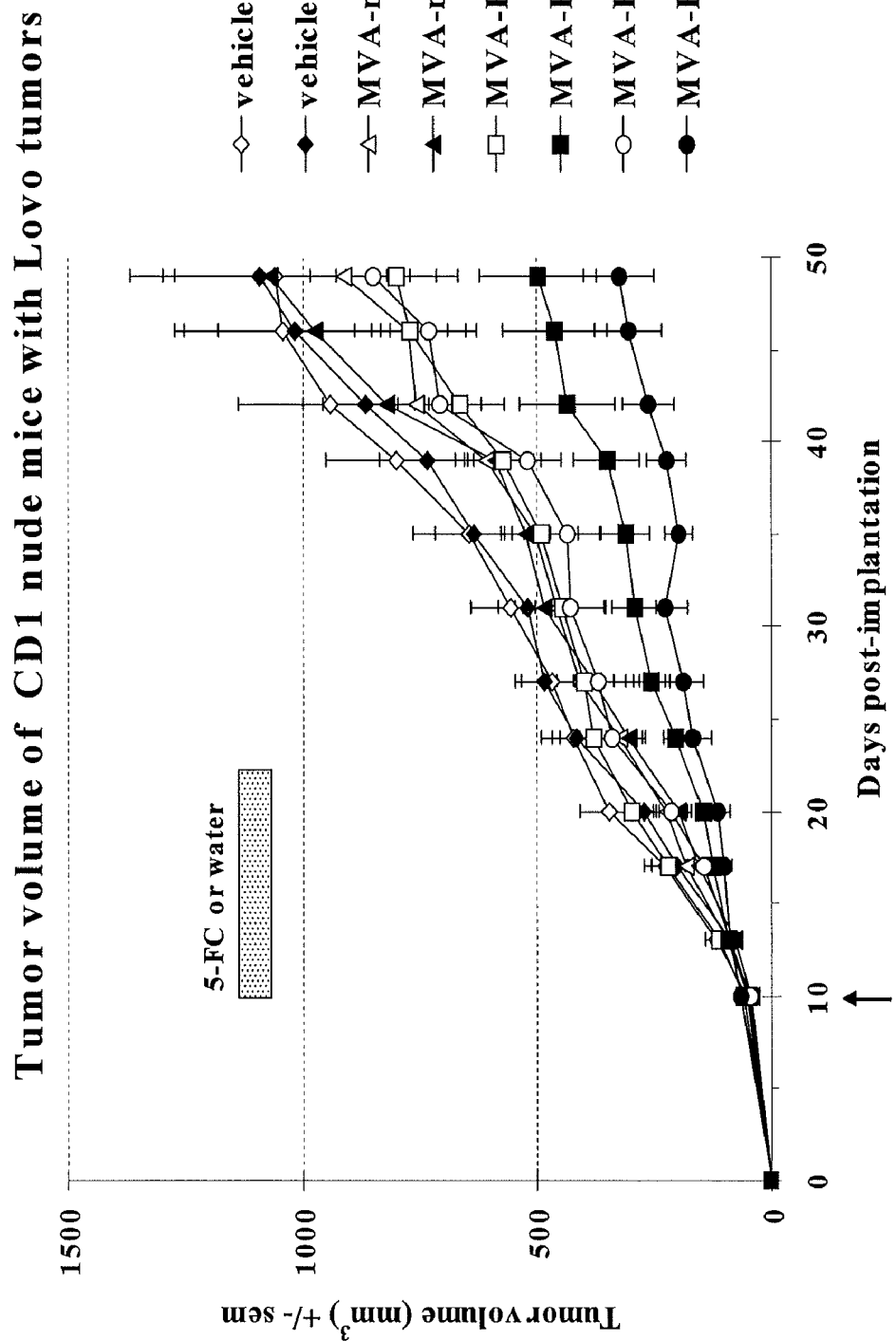

SEQUENCE LISTING

```
<160> NUMBER OF SEQ ID NOS: 2

<210> SEQ ID NO 1
<211> LENGTH: 373
<212> TYPE: PRT
<213> ORGANISM: Artificial Sequence
<220> FEATURE:
<223> OTHER INFORMATION: Description of Artificial Sequence :Fusion
      protein having a CDase activity
<300> PUBLICATION INFORMATION:

<400> SEQUENCE: 1

Met Val Thr Gly Gly Met Ala Ser Lys Trp Asp Gln Lys Gly Met Asp
  1               5                  10                  15

Ile Ala Tyr Glu Glu Ala Ala Leu Gly Tyr Lys Glu Gly Gly Val Pro
             20                  25                  30

Ile Gly Gly Cys Leu Ile Asn Asn Lys Asp Gly Ser Val Leu Gly Arg
         35                  40                  45

Gly His Asn Met Arg Phe Gln Lys Gly Ser Ala Thr Leu His Gly Glu
     50                  55                  60

Ile Ser Thr Leu Glu Asn Cys Gly Arg Leu Glu Gly Lys Val Tyr Lys
 65                  70                  75                  80

Asp Thr Thr Leu Tyr Thr Thr Leu Ser Pro Cys Asp Met Cys Thr Gly
                 85                  90                  95

Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140
```

```
Ile Asp Glu Arg Pro Gln Asp Trp Phe Glu Asp Ile Gly Glu Ala Ser
145                 150                 155                 160

Glu Pro Phe Lys Asn Val Tyr Leu Leu Pro Gln Thr Asn Gln Leu Leu
            165                 170                 175

Gly Leu Tyr Thr Ile Ile Ser Asn Lys Asn Thr Thr Arg Pro Asp Phe
            180                 185                 190

Ile Phe Tyr Ser Asp Arg Ile Ile Arg Leu Leu Val Glu Glu Gly Leu
        195                 200                 205

Asn His Leu Pro Val Gln Lys Gln Ile Val Glu Thr Asp Thr Asn Glu
        210                 215                 220

Asn Phe Glu Gly Val Ser Phe Met Gly Lys Ile Cys Gly Val Ser Ile
225                 230                 235                 240

Val Arg Ala Gly Glu Ser Met Glu Gln Gly Leu Arg Asp Cys Cys Arg
            245                 250                 255

Ser Val Arg Ile Gly Lys Ile Leu Ile Gln Arg Asp Glu Glu Thr Ala
            260                 265                 270

Leu Pro Lys Leu Phe Tyr Glu Lys Leu Pro Glu Asp Ile Ser Glu Arg
        275                 280                 285

Tyr Val Phe Leu Leu Asp Pro Met Leu Ala Thr Gly Gly Ser Ala Ile
        290                 295                 300

Met Ala Thr Glu Val Leu Ile Lys Arg Gly Val Lys Pro Glu Arg Ile
305                 310                 315                 320

Tyr Phe Leu Asn Leu Ile Cys Ser Lys Glu Gly Ile Glu Lys Tyr His
            325                 330                 335

Ala Ala Phe Pro Glu Val Arg Ile Val Thr Gly Ala Leu Asp Arg Gly
            340                 345                 350

Leu Asp Glu Asn Lys Tyr Leu Val Pro Gly Leu Gly Asp Phe Gly Asp
        355                 360                 365

Arg Tyr Tyr Cys Val
        370

<210> SEQ ID NO 2
<211> LENGTH: 216
<212> TYPE: PRT
<213> ORGANISM: Saccharomyces cerevisiae

<400> SEQUENCE: 2

Met Ser Ser Glu Pro Phe Lys Asn Val Tyr Leu Leu Pro Gln Thr Asn
1               5                   10                  15

Gln Leu Leu Gly Leu Tyr Thr Ile Ile Ser Asn Lys Asn Thr Thr Arg
            20                  25                  30

Pro Asp Phe Ile Phe Tyr Ser Asp Arg Ile Ile Arg Leu Leu Val Glu
        35                  40                  45

Glu Gly Leu Asn His Leu Pro Val Gln Lys Gln Ile Val Glu Thr Asp
    50                  55                  60

Thr Asn Glu Asn Phe Glu Gly Val Ser Phe Met Gly Lys Ile Cys Gly
65                  70                  75                  80

Val Ser Ile Val Arg Ala Gly Glu Ser Met Glu Gln Gly Leu Arg Asp
            85                  90                  95

Cys Cys Arg Ser Val Arg Ile Gly Lys Ile Leu Ile Gln Arg Asp Glu
        100                 105                 110

Glu Thr Ala Leu Pro Lys Leu Phe Tyr Glu Lys Leu Pro Glu Asp Ile
    115                 120                 125

Ser Glu Arg Tyr Val Phe Leu Leu Asp Pro Met Leu Ala Thr Gly Gly
    130                 135                 140
```

-continued

```
Ser Ala Ile Met Ala Thr Glu Val Leu Ile Lys Arg Gly Val Lys Pro
145                 150                 155                 160

Glu Arg Ile Tyr Phe Leu Asn Leu Ile Cys Ser Lys Glu Gly Ile Glu
            165                 170                 175

Lys Tyr His Ala Ala Phe Pro Glu Val Arg Ile Val Thr Gly Ala Leu
        180                 185                 190

Asp Arg Gly Leu Asp Glu Asn Lys Tyr Leu Val Pro Gly Leu Gly Asp
        195                 200                 205

Phe Gly Asp Arg Tyr Tyr Cys Val
    210             215
```

POLYPEPTIDE HAVING AN IMPROVED CYTOSINE DEAMINASE ACTIVITY

This application is a divisional of U.S. patent application Ser. No. 10/565,230, filed on Jan. 20, 2006, and issued as U.S. Pat. No. 7,790,445 on Sep. 7, 2010, which is a U.S. National Stage under 35 U.S.C. §371 of International Patent Application PCT/IB2004/002505, filed on Jun. 29, 2004, which claims benefit to U.S. Provisional Patent Application Serial No. 60/508,274, filed on Oct. 6, 2003, which claims priority to European Patent Application No. 03360087.5, filed on Jul. 21, 2003.

The present invention relates to a polypeptide possessing a CDase activity, characterized in that it is derived from a native CDase by addition of an amino acid sequence with the proviso that said polypeptide has no UPRtase or Thymidine Kinase activity.

The invention also relates to a nucleotide sequence which encodes this polypeptide possessing a CDase activity, to a vector for expressing said polypeptide possessing a CDase activity, to a viral particle and a host cell, and to a composition which comprises them. Finally, the invention is also directed towards their therapeutic use and to a method of treatment which implements them. The present invention is particularly useful, within the context of suicide gene therapy, for an application with respect, in particular, to proliferative and infectious diseases.

Gene therapy is defined as being the transfer of genetic information into a host cell or organism. The first protocol applied to man was initiated in the United States, in September 1990, on a patient who was genetically immunodeficient on account of a mutation which affected the gene encoding Adenine Deaminase (ADA). The relative success of this first experiment encouraged the development of this approach for a variety of diseases, including both genetic diseases (with the aim of correcting the malfunction of a defective gene) and acquired diseases (cancers, infectious diseases, such as AIDS, etc.). This technology has experienced a large number of developments since then, including "suicide gene" therapy, which uses genes whose expression products are able to transform an inactive substance (prodrug) into a cytotoxic substance, thereby giving rise to cell death. In 1992, several groups demonstrated the relevance of this novel approach for treating tumors and inhibiting dissemination of the HIV virus, which is responsible for AIDS.

In this respect, the gene encoding the herpes simplex type 1 virus thymidine kinase (HSV-1 TK) constitutes the prototype of the suicide genes (Caruso et al., 1993, Proc. Nati. Acad. Sci. USA 90, 7024-7028; Culver et al., 1992, Science 256, 1550-1552; Ram et al., 1997, Nat. Med. 3, 1354-1361). While the TK polypeptide is not toxic as such, it catalyzes the transformation of nucleoside analogues such as acyclovir or ganciclovir (GCV). The modified nucleosides are incorporated into the DNA chains which are in the process of elongation, inhibiting cell division as a consequence. A large number of suicide gene/prodrug pairs are currently available. Those which may more specifically be mentioned are rat cytochrome p450 and cyclophosphophamide Human Gene Therapy 5, 969-978), *Escherichia coli* (*E. Coli*) purine nucleoside phosphorylase and 6-methylpurine deoxyribonucleoside (Sorscher et al., 1994, Gene Therapy 1, 223-238), *E. coli* guanine phosphoribosyl. transferase and 6-thioxanthine (Mzoz and Moolten, 1993, Human Gene Therapy 4, 589-595) and cytosine deaminase (CDase) and 5-fluorocytosine (5FC).

CDase is involved in the pyrimidine metabolic pathway by which exogenous cytosine is transformed into uracil by means of a hydrolytic deamination. While CDase activities have been demonstrated in prokaryotes and lower eukaryotes (fund and Lacroute, 1970, J. Bacteriol. 102, 607-615; Beck et al., 1972, J. Bacteriol. 110, 219-228; De Haan et al., 1972, Antonie van Leeuwenhoek 38, 257-263; Hoeprich et al., 1974, J. Inf. Dis. 130, 112-118; Esders and Lynn, 1985, J. Biol. Chem. 260, 3915-3922), they are not present in mammals (Koechlin et al., 1966, Biochem Pharmacol. 15, 435-446; Polak et al., 1976, Chemotherapy 22, 137-153). The *Saccharomyces cerevisiae* (*S. cerevisiae*) FCY1 and the *E. coli* codA genes, which respectively encode the CDase of these two organisms, are known and their sequences have been published (EP 402 108; Erbs et al., 1997, Curr. Genet. 31, 1-6; WO93/01281).

CDase also deaminates an analogue of cytosine, i.e. 5-fluorocytosine (5-FC), thereby forming 5-fluorouracil (5-FU), which is a compound which is highly cytotoxic when it is converted into 5-fluoro-UMP (5-FUMP). Cells which lack CDase activity, either because of a mutation which inactivates the gene encoding the enzyme or because they are naturally deficient in this enzyme, as are mammalian cells, are resistant to 5-FC (fund and Lacroute, 1970, J. Bacteriol, 102, 607-615; Kilstrup et al., 1989, J. Bacteriol. 1989 171, 2124-2127). By contrast, mammalian cells into which the sequences encoding CDase activity were transferred became sensitive to 5-FC (Huber et al., 1993, Cancer Res. 53, 4619-4626; Mullen et al., 1992, Proc. Natl. Acad. Sci. USA 89, 33-37; WO93/01281). In addition, the neighboring, untransformed cells also become sensitive to 5-FC (Huber et al., 1994, Proc. Natl. Acad. Sci. USA 91, 8302-8306). This phenomenon, which is termed a bystander effect, is due to the cells which are expressing the CDase activity secreting 5-FU, which then intoxicates the neighboring cells by straightforward diffusion across the plasma membrane. This property of 5-FU in diffusing passively represents an advantage as compared with the tk/GCV reference system, where the bystander effect requires there to be contact with the cells which are expressing tk (Mesnil et al., 1996, Proc. Natl. Acad. Sci. USA 93, 1831-1835). All the advantages which CDase offers within the context of gene therapy, in particular anticancer gene therapy, can therefore be readily understood.

In order to improve the efficiency of methods using CDase activity, the prior art document WO-A-96/16183 recommends using a fusion protein which encodes a two-domain enzyme possessing CDase and UPRTase activities, and demonstrates in vitro that the transfer of a hybrid codA::upp or FCY1::FUR1 gene, carried by an expression plasmid, increases the sensitization of transfected B16 cells to 5-FC. WO99/54481 provides an improvement of this invention by using a mutated FUR1 gene which encodes a UPRTase which is deleted in its N-terminal part.

The present invention is an improvement of the earlier techniques in that it used a polypeptide possessing a CDase activity, characterized in that it is derived from a native CDase by addition of an amino acid sequence, with the proviso that said polypeptide has no UPRtase or thymidine kinase activity.

The present invention provides a more efficient polypeptide, thereby making it possible to increase the sensitivity of cells to 5-FC or the bystander effect induced by the production of 5-FU and to improve the prospects for gene therapy using suicide genes. This mutant can be used for a large number of applications, in particular anticancer and antiviral applications, and all applications which require cell death.

"Cytosine deaminase activity" (CDase activity) is understood as covering the deamination of cytosine or one of its analogs.

"derives from a native CDase" widely means that said polypeptide possessing a CDase activity comprises an amino acid sequence which has a degree of identity which is greater than 70%, advantageously greater than 80%, preferably greater than 90% and, very preferably greater than 95% with said native CDase. Still more preferably, the polypeptide possessing a CDase activity comprises the amino acid sequence of a native CDase.

Within the meaning of the present invention, a native CDase refers to a CDase of prokaryotic or eukaryotic origin. Preferably, the CDase is a yeast CDase, in particular that encoded by the *Saccharomyces cerevisiae* FCY1 gene. The cloning and the sequence of the genes encoding the CDases of different origins are available in the literature and the specialized databases. For information, the sequence of the FCY1 gene is disclosed in Erbs et al. (1997, Curr. Genet. 31, 1-6).

A preferred example is a native CDase which comprises an amino acid sequence which is substantially as depicted in SEQ ID NO: 1 sequence identifier, starting at the Met residue in position 1 and finishing at the Glu residue in position 158. The term "substantially" refers to a degree of identity with said SEQ ID NO: 1 sequence which is greater than 70%, advantageously greater than 80%, preferably greater than 90% and, very preferably greater than 95%. Still more preferably, the polypeptide comprises the amino acid sequence depicted in SEQ ID NO: 1 sequence identifier starting at the Met residue in position 1 and finishing at the Glu residue in position 158. A polypeptide having the amino acid sequence as depicted in SEQ ID NO: 1 sequence identifier starting at the Met residue in position 1 and finishing at the Glu residue in position 158 is very particularly appropriate for implementing the invention.

According to an advantageous embodiment, a polypeptide according to the invention exhibits a CDase activity which is appreciably higher than that of said native CDase. Thus, the examples which follow demonstrate that the addition of an amino acid sequence which has no UPRtase activity makes it possible to increase the sensitization of the target cells to 5-FC and/or the bystander effect induced in the treated animal. The factor by which the sensitization is increased is advantageously at least 2, preferably at least 5 and, very preferably, 10 or more.

"Polypeptide which has no UPRtase activity" encompasses polypeptide which are unable to convert 5-FU in 5-FUMP. The ability of an amino acid sequence to convert 5-FU in 5-FUMP can be assessed by using the method disclosed in the working example of the present application.

"polypeptide which has no thymidine kinase activity" encompasses polypeptide which are unable to phosphorylate nucleosides (e.g., dT) and nucleoside analogues such as ganciclovir (9-{[2-hydroxy-1-(hydroxymethyl)ethoxy] methyl}guanosine), famciclovir, buciclovir, penciclovir, valciclovir, acyclovir (9-[2-hydroxy ethoxy)methyl]guanosine), trifluorothymidine, 1-[2-deoxy, 2-fluoro, beta-D-arabino furanosyl]-5-iodouracil, ara-A (adenosine arabinoside, vivarabine), 1-beta-D-arabinofuranoxyl thymine, 5-ethyl-2'-deoxyuridine, 5-iodo-5'-amino-2,5'-dideoxyuridine, idoxuridine (5-iodo-2'-deoxyuridine), AZT (3' azido-3' thymidine), ddC (dideoxycytidine), AIU (5-iodo-5' amino 2',5'-dideoxyuridine) and AraC (cytidine arabinoside).

According to a preferred embodiment, the amino acid sequence added to the native CDase, is between 10 and 1000, more preferably between 100 and 400 and very preferably between 200 and 300 amino acid length. Even though the addition can take place at any site in the native CDase, the N-or C-terminal ends are preferred, in particular the C-terminal end.

Advantageously, the amino acid sequence which added to the native CDase, is derived from a polypeptide having an UPRTase activity.

"Derived from a polypeptide having an UPRtase activity" widely means that said amino acid sequence has a degree of identity which is greater than 70%, advantageously greater than 80%, preferably greater than 90% and, very preferably greater than 95% with the amino acid sequence of a polypeptide having an UPRTase activity.

Within the meaning of the present invention, a polypeptide possessing a UPRTase activity refers to a polypeptide which is able to convert uracil, or one of its derivatives, into a monophosphate analog, in particular 5-FU into 5-FUMP. "Mutation" is to be understood as being the addition, deletion and/or substitution of one or more residues at any site in said polypeptide.

The polypeptide having an UPRtase activity from which the amino acid sequence according to the invention may derives can be of any origin, in particular of prokaryotic, fungal or yeast origin. By way of illustration, the UPRTases from *E. coli* (Anderson et al., 1992, Eur. J. Biochem 204, 51-56), from *Lactococcus lactis* (Martinussen and Hammer, 1994, J. Bacteriol. 176, 6457-6463), from *Mycobacterium bovis* (Kim et al., 1997, Biochem Mol. Biol. mt 41, 1117-1124) and from *Bacillus subtilis* (Martinussen et al., 1995, J. Bacteriol. 177, 271-274), can be used within the context of the invention. However, very particular preference is given to using a yeast UPRTase, in particular that encoded by the *S. cerevisiae* FUR1 gene, whose sequence is disclosed in Kern et al. (1990, Gene 88, 149-157). More particularly, by way of information, the sequences of the genes, and those of the corresponding UPRTases, can be found in the literature and in specialized databases (SWISSPROT, EMBL, Genbank, Medline, etc.). More particularly, mutants encoded by the fur 1-7, fur 1-8 and fur 1-9 can be used in the present invention. In a preferred embodiment, the amino acid sequence which derives from a polypeptide having an UPRTase activity is the amino acid sequences encoded by the fur 1-8 allele (Kern et al., 1990, Gene 88, 149-157).

According to one particularly advantageous embodiment, the amino acid sequence, added to the native CDase, according to the invention derives from a deletion mutant of a native UPRTase. The deletion is preferably located in the N-terminal region of the original UPRTase. The deletion can be total (affecting all the residues of said N-terminal region) or partial (affecting one or more residues which may or may not be continuous in the primary structure). In a general manner, a polypeptide consists of an N-terminal part, of a central part and of a C-terminal part, with each part representing approximately one third of the molecule. For example, in the case of the *S. cerevisiae* UPRTase, which contains 251 amino acids, the N-terminal part consists of the first 83 residues, starting with the so-called initiating methionine, which is located in the first position of the native form. In the case of the *E. coli* UPRTase, the N-terminal part covers positions 1 to 69.

It has been shown that the expression product of the mutant gene, designated FUR1Δ105, is able to complement an *S. cerevisiae* fur1 mutant, thereby demonstrating that it is functional.

Very preferably, polypeptide having an UPRTase activity according to the invention is derived from a native UPRTase at least by deleting all or part of the N-terminal region upstream of the second ATG codon of said native UPRTase. The total deletion of the aforesaid region is preferred. For example, the UPRTase encoded by the FUR1 gene comprises a first ATG codon (initiating ATG codon) in position +1 followed by a second in position +36. Thus, it is possible to envisage deleting residues +1 to 35 within the context of the present invention, thereby giving a polypeptide which starts at the methionine which is normally found in position +36 of the native form. It has been shown that the expression product of the mutant gene, designated FUR1Δ105, is able to complement an S. cerevisiae fur1 mutant, thereby demonstrating that it is functional.

A preferred amino acid sequence, added to the native CDase, according to the invention comprises an amino acid sequence which is substantially as depicted in SEQ ID NO: 2 sequence identifier, starting at the Ser residue in position 2 and finishing at the Val residue in position 216. The term "substantially" refers to a degree of identity with said sequence which is greater than 70%, advantageously greater than 80%, preferably greater than 90% and, very preferably greater than 95%. Still more preferably, the amino acid sequence, added to the native CDase, comprises the amino acid sequence depicted in SEQ ID NO:2 sequence identifier starting at the Ser residue in position 2 and finishing at the Val residue in position 216. A amino acid sequence, added to the native CDase, having the amino acid sequence as depicted in SEQ ID NO: 2 sequence identifier starting at the Ser residue in position 2 and finishing at the Val residue in position 216 is very particularly appropriate for implementing the invention. This amino acid sequence, added to the native CDase, can contain additional mutations. Substitution of the serine residue in position 2 of SEQ ID NO:2 sequence identifier with an Alanine residue may in particular be mentioned.

A preferred polypeptide possessing a CDase activity according to the invention comprises an amino acid sequence which is substantially as depicted in SEQ ID NO: 1 sequence identifier, starting at the Met residue in position 1 and finishing at the Val residue in position 373. The term "substantially" refers to a degree of identity with said SEQ ID NO: 1 sequence which is greater than 70%, advantageously greater than 80%, preferably greater than 90% and, very preferably greater than 95%. Still more preferably, the polypeptide comprises the amino acid sequence depicted in SEQ ID NO: 1 sequence identifier starting at the Met residue in position 1 and finishing at the Val residue in position 373. A polypeptide having the amino acid sequence as depicted in SEQ ID NO: 1 sequence identifier starting at the Met residue in position 1 and finishing at the Val residue in position 373 is very particularly appropriate for implementing the invention.

In a general manner, a polypeptide according to the invention can be produced either by the conventional methods of chemical synthesis or by recombinant DNA techniques (see, for example, Maniatis et al., 1989, *Laboratory Manual*, Cold Spring Harbor, Laboratory Press, Cold Spring Harbor, N.Y.). For this reason, the present invention also covers a preparation process in which a nucleotide sequence encoding said polypeptide is introduced into a cell in order to generate a transformed cell, said transformed cell is cultured under conditions appropriate for enabling said polypeptide to be produced, and said polypeptide is harvested from the cell culture. The producer cell can be of any origin and, without limitation, a bacterium, a yeast or a mammalian cell, to the extent that the nucleotide sequence under consideration is either integrated into its genome or integrated into, an appropriate expression vector which is able to replicate. Naturally, the nucleotide sequence is placed under the control of transcription and translation signals which enable it to be expressed in the producer cell. Expression vectors and control signals are known to the skilled person. The polypeptide can be recovered from the medium or the cells (after they have been lyzed) and subjected to conventional purification steps (by chromatography, electrophoresis, filtration, immunopurification, etc.).

The present invention also relates to a nucleotide sequence which encodes a polypeptide according to the invention. The nucleotide sequence can be a cDNA or genomic sequence or be of a mixed type. It can, where appropriate, contain one or more introns, with these being of native, heterologous (for example the intron of the rabbit β-globin gene, etc.) or synthetic origin, in order to increase expression in the host cells. The sequences employed within the context of the present invention can be obtained by the conventional techniques of molecular biology, for example by screening libraries with specific probes, by immunoscreening expression libraries or by PCR using suitable primers, or by chemical synthesis. The mutants can be generated from the native sequences by substituting, deleting and/or adding one or more nucleotides using the techniques of site-directed mutagenesis, of PCR, of digesting with restriction and ligation enzymes, or else by chemical synthesis. The ability of the mutants and constructs to function can be verified by assaying the enzymatic activity or by measuring the sensitivity of target cells to 5-FC and/or 5-FU.

The present invention also relates to a recombinant vector which carries a nucleotide sequence according to the invention which is placed under the control of the elements which are required for expressing it in a host cell. The recombinant vector can be of plasmid or viral origin and can, where appropriate, be combined with one or more substances which improve the transfectional efficiency and/or stability of the vector. These substances are widely documented in the literature which is available to the skilled person (see, for example, Feigner et al., 1987, Proc. West. Pharmacol. Soc. 32, 115-121; Hodgson and Solaiman, 1996, Nature Biotechnology 14, 339-342; Remy et al., 1994, Bioconjugate Chemistry, 5, 647-654). By way of non-limiting illustration, the substances can be polymers, lipids, in particular cationic lipids, liposomes, nuclear proteins or neutral lipids. These substances can be used alone or in combination. A combination which can be envisaged is that of a recombinant plasmid vector which is combined with cationic lipids (DOGS, DC-CHOL, spermine-chol, spermidine-chol, etc.), lysophospholipides (for example Hexadecylphosphocholine) and neutral lipids (DOPE).

According to a preferred embodiment, the cationic lipids which can be used in the present invention are the cationic lipids describes in EP901463B1 and more preferably pcTG90.

The choice of the plasmids which can be used within the context of the present invention is immense. They can be cloning vectors and/or expression vectors. In a general manner, they are known to the skilled person and, while a number of them are available commercially, it is also possible to construct them or to modify them using the techniques of genetic manipulation. Examples which may be mentioned are the plasmids which are derived from pBR322 (Gibco BRL), pUC (Gibco BRL), pBluescript (Stratagene), pREP4, pCEP4 (Invitrogene) or p Poly (Lathe et al., 1987, Gene 57, 193-201). Preferably, a plasmid which is used in the context of the present invention contains an origin of replication which ensures that replication is initiated in a producer cell and/or a host cell (for example, the ColE1 origin will be chosen for a plasmid which is intended to be produced in *E. coli* and the oriP/EBNA1 system will be chosen if it desired that the plasmid should be self-replicating in a mammalian host cell, Lupton and Levine, 1985, Mol. Cell. Biol. 5, 2533-2542; Yates et al., Nature 313, 812-815). The plasmid can additionally comprise a selection gene which enables the transfected cells to be selected or identified (complementation of an auxotrophic mutation, gene encoding resistance to an antibiotic, etc.). Naturally, the plasmid can contain additional elements which improve its maintenance and/or its stability in a given cell (cer sequence, which promotes maintenance of a plasmid in monomeric form (Summers and Sherrat, 1984, Cell 36, 1097-1103, sequences for integration into the cell genome).

With regard to a viral vector, it is possible to envisage a vector which is derived from a poxvirus (vaccinia virus, in particular MVA, canarypoxvirus, etc.), from an adenovirus, from a retrovirus, from a herpesvirus, from an alphavirus, from a foamy virus or from an adenovirus-associated virus. It is possible to use replication competent or replication deficient viral vectors. Preference will be given to using a vector which does not integrate. In this respect, adenoviral vectors and MVA are very particularly suitable for implementing the present invention.

According to a preferred embodiment, the viral vector according to the invention derives from a Modified Vaccinia Virus Ankara (MVA). Mva vectors and methods to produce such vectors are fully described in European patents EP83286 and EP206920, as well as in Mayr et al. (1975, Infection 3, 6-14) and Sutter et Moss (1992, Proc. Natl. Acad. Sci. USA 89, 10847-10851). According to a more preferred embodiment, the nucleotide sequence according to the invention may be inserted in deletion I, II, III, IV, V and VI of the MVA vector and even more preferably in deletion III (Meyer et al., 1991, J. Gen. Virol. 72, 1031-1038; Sutter et al., 1994, Vaccine 12, 1032-1040).

Retroviruses have the property of infecting, and in most cases integrating into, dividing cells and in this regard are particularly appropriate for use in relation to cancer. A recombinant retrovirus according to the invention generally contains the LTR sequences, an encapsidation region and the nucleotide sequence according to the invention, which is placed under the control of the retroviral LTR or of an internal promoter such as those described below. The recombinant retrovirus can be derived from a retrovirus of any origin (murine, primate, feline, human, etc.) and in particular from the M0MuLV (Moloney murine leukemia virus), MVS (Murine sarcoma virus) or Friend murine retrovirus (Fb29). It is propagated in an encapsidation cell line which is able to supply in trans the viral polypeptides gag, pol and/or env which are required for constituting a viral particle. Such cell lines are described in the literature (PA317, Psi CRIP GP +Am-12 etc.). The retroviral vector according to the invention can contain modifications, in particular in the LTRs (replacement of the promoter region with a eukaryotic promoter) or the encapsidation region (replacement with a heterologous encapsidation region, for example the VL3O type) (see French applications 94 08300 and 97 05203)

Preference will be also given to using an adenoviral vector which lacks all or part of at least one region which is essential for replication and which is selected from the E1, E2, E4 and L1-L5 regions in order to avoid the vector being propagated within the host organism or the environment. A deletion of the E1 region is preferred. However, it can be combined with (an)other modification(s)-/deletion(s) affecting, in particular, all or part of the E2, E4 and/or L1-L5 regions, to the extent that the defective essential functions are complemented in trans by means of a complementing cell line and/or a helper virus. In this respect, it is possible to use second-generation vectors of the state of the art (see, for example, international applications WO-A-94/28152 and WO-A-97/04119). By way of illustration, deletion of the major part of the E1 region and of the E4 transcription unit is very particularly advantageous. For the purpose of increasing the cloning capacities, the adenoviral vector can additionally lack all or part of the nonessential E3 region. According to another alternative, it is possible to make use of a minimal adenoviral vector which retains the sequences which are essential for encapsidation, namely the 5' and 3' ITRs (Inverted Terminal Repeat), and the encapsidation region. The various adenoviral vectors, and the techniques for preparing them, are known (see, for example, Graham and Prevect, 1991, in Methods in Molecular Biology, Vol 7, p 109-128; Ed: E. J. Murey, The Human Press mc).

Furthermore, the origin of the adenoviral vector according to the invention can vary both from the point of view of the species and from the point of view of the serotype. The vector can be derived from the genome of an adenovirus of human or animal (canine, avian, bovine, murine, ovine, porcine, simian, etc.) origin or from a hybrid which comprises adenoviral genome fragments of at least two different origins. More particular mention may be made of the CAV-1 or CAV-2 adenoviruses of canine origin, of the DAV adenovirus of avian origin or of the Bad type 3 adenovirus of bovine origin (Zakharchuk et al., Arch. Virol., 1993, 128: 171-176; Spibey and Cavanagh, J. Gen. Virol. 1989, 70: 165-172; Jouvenne et al., Gene, 1987, 60: 21-28; Mittal et al., J. Gen. Virol., 1995, 76: 93-102). However, preference will be given to an adenoviral vector of human origin which is preferably derived from a serotype C— adenovirus, in particular a type 2 or 5 serotype C adenovirus.

The term "replication-competent" as used herein refers to a viral vector capable of replicating in a host cell in the absence of any transcomplementation. In the context of the present invention, this term also encompasses replication-selective or conditionally-replicative adenoviral vectors which are engineered to replicate better or selectively in cancer or hyperproliferative host cells.

According to a preferred embodiment of the invention, the replication competent vector is a replication competent adenoviral vector. These replication competent adenoviral vectors are well known by the one skilled in the art. Among these, adenoviral vectors deleted in the E1b region coding the 55 kD P53 inhibitor, as in the ONYX-015 virus (Bischoff et al, 1996; Heise et al., 2000; WO 94/18992), are particularly preferred. Accordingly, this virus can be used to selectively infect and kill p53-deficient neoplastic cells. A person of ordinary skill in the art can also mutate and disrupt the p53 inhibitor gene in adenovirus 5 or other viruses according to established techniques. Adenoviral vectors deleted in the E1A Rb binding region can also be used in the present invention. For example, Delta24 virus which is a mutant adenovirus carrying a 24 base pair deletion in the E1A region (Fueyo et al., 2000). Delta24 has a deletion in the Rb binding region and does not bind to Rb. Therefore, replication of the mutant virus is inhibited by Rb in a normal cell. However, if Rb is inactivated and the cell becomes neoplastic, Delta24 is no longer inhibited. Instead, the mutant virus replicates efficiently and lyses the Rb-deficient cell.

An adenoviral vector according to the present invention can be generated in vitro in *Escherichia coli* (*E. coli*) by ligation or homologous recombination (see, for example, international application WO-A-96/17070) or else by recombination in a complementing cell line.

The elements required for expression consist of all the elements which enable the nucleotide sequence to be transcribed into RNA and the mRNA to be translated into polypeptide. These elements comprise, in particular, a promoter which may be regulable or constitutive. Naturally, the promoter is suited to the chosen vector and the host cell.

Examples which may be mentioned are the eukaryotic promoters of the PGK (phosphoglycerate kinase), MT (metallothionein; McIvor et al., 1987, Mol. Cell Biol. 7, 838-848), α-1 antitrypsin, CFTR, surfactant, immunoglobulin, β-actin (Tabin et al., 1982, Mol. Cell Biol. 2, 426-436) and SRa (Takebe et al., 1988, Mol. Cell Biol. 8, 466-472) genes, the early promoter of the SV40 virus (Simian virus), the LTR of RSV (Rous sarcoma virus), the HSV-1 TK promoter, the early promoter of the CMV virus (Cytomegalovirus)., the p7.5K pH5R, pK1L, p28 and p11 promoters of the vaccinia virus, and the E1A and MLP adenoviral promoters. The promoter can also be a promoter which stimulates expression in a tumor or cancer cell. Particular mention may be made of the promoters of the MUC-1 gene, which is overexpressed in breast and prostate cancers (Chen et al., 1995, J. Clin. Invest. 96, 2775-2782), of the CEA (standing for carcinoma embryonic antigen) gene, which is overexpressed in colon cancers (Schrewe et al., 1990, Mol. Cell. Biol. 10, 2738-2748) of the tyrosinase gene, which is overexpressed in melanomas (Vile et al., 1993, Cancer Res. 53, 3860-3864), of the ERBB-2 gene, which is overexpressed in breast and pancreatic cancers (Harris et al., 1994, Gene Therapy 1, 170-175) and of the α-fetoprotein gene, which is overexpressed in liver cancers (Kanai et al., 1997, Cancer Res. 57, 461-465). The cytomegalovirus (CMV) early promoter is very particularly preferred.

However, when a vector deriving from a Vaccinia Virus (as for example an MVA vector) is used, the promoter of the thymidine kinase 7.5K gene is particularly preferred.

The necessary elements can furthermore include additional elements which improve the expression of the nucleotide sequence according to the invention or its maintenance in the host cell. Intron sequences, secretion signal sequences, nuclear localization sequences, internal sites for the reinitiation of translation of IRES type, transcription termination poly A sequences, tripartite leaders and origins of replication may in particular be mentioned. These elements are known to the skilled person.

The recombinant vector according to the invention can also comprise one or more additional genes of interest, with it being possible for these genes to be placed under the control of the same regulatory elements (polycistronic cassette) or of independent elements. Genes which may in particular be mentioned are the genes encoding interleukins IL-2, IL-4, IL-7, IL-10 and IL-12, interferons, tumor necrosis factor (TNF), colony stimulating factors (CSF), in particular GM-CSF, and factors acting on angiogenesis (for example PA1-1, standing for plasminogen activator inhibitor). In one particular embodiment, the recombinant vector according to the invention comprises the gene of interest encoding IL-2 or encoding interferon γ (INFγ). It is also possible to envisage combining the nucleotide sequence according to the invention with other suicide genes such as the HSV-1 TK gene, the ricin gene, the cholera toxin gene, etc.

The present invention also relates to a viral particle which comprises a recombinant vector according to the invention. Such a viral particle can be generated from a viral vector using any technique which is conventional in the field of the art. The viral particle is propagated in a complementing cell which is suited to the deficiencies of the vector. With regard to an adenoviral vector, use will, for example, be made of the 293 cell line, which was established using human embryonic kidney cells and which efficiently complements the E1 function (Graham et al., 1977, J. Gen. Virol. 36, 59-72), of the A549-E1 cell line (Imler et al., 1996, Gene Therapy 3, 75-84) or of a cell line which permits double complementation (Yeh et al., 1996, J. Virol. 70, 559-565; Krougliak and Graham, 1995, Human Gene Therapy 6, 1575-1586; Wang et al., 1995 Gene Therapy 2, 775-783; international application WO 97/04119). It is also possible to employ helper viruses to at least partially complement the defective functions. A complementing cell is understood as being a cell which is able to supply in trans the early and/or late factors which are required for encapsidating the viral genome in a viral capsid in order to generate a viral particle which contains the recombinant vector. Said cell may not be able to complement all the defective functions of the vector on its own and, in this case, can be transfected/transduced with a vector/helper virus which supplies the additional functions.

The invention also relates to a process for preparing a viral particle, in which process:
(i) a recombinant vector according to the invention is introduced into a complementing cell which is able to complement said vector in trans, so as to obtain a transfected complementing cell,
(ii) said transfected complementing cell is cultured under conditions which are appropriate for enabling said viral particle to be produced, and
(iii) said viral particle is recovered from the cell culture.

While the viral particle can of course be recovered from the culture supernatant, it can also be recovered from the cells. One of the commonly employed methods consists in lysing the cells by means of consecutive freezing/thawing cycles in order to collect the virions in the lysis supernatant. The virions can then be amplified and purified using the techniques of the art (chromatographic method, method of ultra-centrifugation, in particular through a cesium chloride gradient, etc.).

The present invention also relates to a host cell which comprises a nucleotide sequence or a recombinant vector according to the invention, or is infected with a viral particle according to the invention. For the purposes of the present invention, a host cell consists of any cell which can be transfected with a recombinant vector or can be infected with a viral particle, as defined above. A mammalian cell, in particular a human cell is very particularly suitable. The cell can comprise said vector in a form which is or is not (episome) integrated into the genome. The cell can be a primary or tumor cell of any origin, in particular an hematopoietic cell (totipotent stem cell, leukocyte, lymphocyte, monocyte or macrophage, etc.), muscle cell (satellite cell, myocyte, myoblast, smooth muscle cell, etc.), cardiac cell, pulmonary cell, tracheal cell, hepatic cell, epithelial cell or fibroblast.

The present invention, also relates to a composition which comprises a polypeptide, a nucleotide sequence, a recombinant vector, a viral particle or a host cell according to the invention in combination with a pharmaceutically acceptable excipient The present invention furthermore relates to a composition which comprises a polypeptide according to the invention and a polypeptide of interest which is encoded by one of the previously mentioned genes of interest. Of these polypeptides of interest, particular mention may be made of interleukins IL-2, IL-4, IL-7, IL-10 and IL-12, interferons, tumor necrosis factor (TNF), colony stimulating factors (CSF), in particular GM-CSF, and factors acting on angiogenesis (for example. PA1-1, standing for plasminogen activator inhibitor) IL-2 or INFγ are very particularly envisaged.

The composition can also be based on nucleotide sequences which enable the above polypeptides to be expressed within the host cell. The nucleotide sequences may be carried by one and the same expression vector or by two independent vectors. Said composition can of course comprise viral particles which are generated from (a) viral vector(s) expressing said nucleotide sequence(s).

The present invention additionally relates to a composition which comprises a nucleotide sequence according to the invention and a second nucleotide sequence of interest which encodes a polypeptide selected from IL-2 and INFγ.

A composition according to the invention is more specifically intended for the preventive or curative treatment of diseases by means of gene therapy and is more specifically aimed at proliferative diseases (cancers, tumors, restenosis, etc.) and at diseases of infectious origin, in particular of viral origin (induced by hepatitis B or C viruses, HIV, herpes, retroviruses, etc.).

A composition according to the invention can be made conventionally with a view to administering it locally, parenterally or by the digestive route. In particular, a therapeutically effective quantity of the therapeutic or prophylactic agent is combined with a pharmaceutically acceptable excipient. It is possible to envisage a large number of routes of administration. Examples which may be mentioned are the intragastric, subcutaneous, intracardiac, intramuscular, intravenous, intraperitoneal, intratumor, intranasal, intrapulmonary and intratracheal routes. In the case of these three latter embodiments, it is advantageous for administration to take place by means of an aerosol or by means of instillation. The administration can take place as a single dose or as a dose which is repeated on one or more occasions after a particular time interval. The appropriate route of administration and dosage vary depending on a variety of parameters, for example the individual, the disease to be treated or the gene(s) of interest to be transferred. The preparations based on viral particles according to the invention can be formulated in the form of doses of between $10^4$ and $10^{14}$ pfu (plaque-forming units), advantageously $10^5$ and $10^{13}$ pfu, preferably $10^6$ and $10^{12}$ pfu, more preferably $10^9$ and $10^{10}$ when adenoviral particles are used and $10^6$ and $10^7$ when MVA particles are used. As far as the recombinant vector according to the invention is concerned, it is possible to envisage doses comprising from 0.01 to 100 mg of DNA, preferably from 0.05 to 10 mg, very particularly preferably from 0.5 to 5 mg. A composition based on polypeptides preferably comprises from 0.05 to 10 g, very particularly preferably from 0.05 to 5 g, of said polypeptide. Naturally, the doses can be adjusted by the clinician.

The formulation can also include a diluent, an adjuvant or an excipient which is acceptable from the pharmaceutical point of view, as well as solubilizing, stabilizing and preserving agents. In the case of an injectable administration, preference is given to a formulation in an aqueous, non-aqueous or isotonic solution. It can be presented as a single dose or as a multidose, in liquid or dry (powder, lyophilizate, etc.) form which can be reconstituted at the time of use using an appropriate diluent. The formulation can also comprise appropriate quantities of prodrugs.

The present invention also relates to the therapeutic or prophylactic use of a polypeptide, of a recombinant vector, of a viral particle or of a host cell according to the invention for preparing a medicament which is intended for treating the human or animal body by gene therapy or by administering protein which has been produced by the recombinant route. According to a first possibility, the medicament can be administered directly in vivo (for example by intravenous injection, into an accessible tumor, into the lungs by means of an aerosol, into the vascular system using an appropriate catheter, etc.). It is also possible to adopt the ex vivo approach, which consists in removing cells from the patient (bone marrow stem cells, peripheral blood lymphocytes, muscle cells, etc.), transfecting or infecting them in vitro in accordance with the techniques of the art and then readministering them to the patient. A preferred use consists in treating or preventing cancers, tumors and diseases which result from unwanted cell proliferation. Conceivable applications which may be mentioned are cancers of the breast, of the uterus (in particular those induced by papilloma viruses), of the prostate, of the lung, of the bladder, of the liver, of the colon, of the pancreas, of the stomach, of the esophagus, of the larynx, of the central nervous system (e.g. glioblastoma) and of the blood (lymphomas, leukemia, etc.). It can also be used in the context of cardiovascular diseases, for example in order to inhibit or retard the proliferation of the smooth muscle cells of the blood vessel wall (restenosis). Finally, in the case of infectious diseases, it is possible to conceive of the medicament being applied to AIDS.

The invention also extends to a method for treating diseases by gene therapy, characterized in that a nucleotide sequence, a recombinant vector, a viral particle or a host cell according to the invention is administered to an host organism or cell which is in need of such treatment.

According to an advantageous embodiment, the therapeutic use or the treatment method also comprises an additional step in which pharmaceutically acceptable quantities of a prodrug, advantageously an analog of cytosine, in particular 5-FC, are administered to the host organism or cell. By way of illustration, it is possible to use a dose of from 50 to 500 mg/kg/day, with a dose of 200 mg/kg/day being preferred. Within the context of the present invention, the prodrug is administered in accordance with standard practice (e.g. per os, systematically), with the administration taking place prior to, concomitantly with or else subsequent to the administration of the therapeutic agent according to the invention. The oral route is preferred. It is possible to administer a single dose of prodrug or doses which are repeated for a time which is sufficiently long to enable the toxic metabolite to be produced within the host organism or cell.

Furthermore, the composition or method according to the invention can be combined with one or more substances which potentiate the cytotoxic effect of the 5-FU. Mention may in particular be made of drugs which inhibit the enzymes of the pathway for the de novo biosynthesis of the pyrimidines (for example those mentioned below), drugs such as Leucovorin (Waxman et al., 1982, Eur. J. Cancer Clin. Oncol. 18, 685-692), which, in the presence of the product of the metabolism of 5-FU (5-FdUMP), increases the inhibition of thymidylate synthase, resulting in a decrease in the pool of dTMP, which is required for replication, and finally drugs such as methotrexate (Cadman et al., 1979, Science 250, 1135-1137) which, by inhibiting dihydrofolate reductase and increasing the pool of PRPP (phosphoribosylpyrophosphate), brings about an increase in the incorporation of 5-FU into the cellular RNA.

The composition or method according to the invention can be combined with one or more substances effective in anticancer therapy. Among pharmaceutical substances effective in anticancer therapy which may be used in association or in combination with the compositions according to the invention, there may be mentioned alkylating agents such as, e.g., mitomycin C, cyclophosphamide, busulfan, ifosfamide, isosfamide, melphalan, hexamethylmelamine, thiotepa, chlorambucil, or dacarbazine; antimetabolites such as, e.g., gemcitabine, capecitabine, 5-fluorouracil, cytarabine, 2-fluorodeoxy cytidine, methotrexate, idatrexate, tomudex or trimetrexate; topoisomerase II inhibitors such as, e.g., doxorubicin, epirubicin, etoposide, teniposide or mitoxantrone; topoisomerase I inhibitors such as, e.g., irinotecan (CPT-11), 7-ethyl-10-hydroxy-camptothecin (SN-38) or topotecan; antimitotic drugs such as, e.g., paclitaxel, docetaxel, vinblastine, vincristine or vinorelbine; and platinum derivatives such as, e.g., cisplatin, oxaliplatin, spiroplatinum or carboplatinum.

The compositions or methods according to the invention can also be use in combination with a radiotherapy.

The present invention is also directed towards using the sequences or recombinant vectors according to the invention as positive selection markers in mammalian cells. Advantageously, the cells are transfected and the cell mixture is then cultured in the presence of inhibitors of the pathway for the de novo biosynthesis of pyrimidines, such as PALA (N-(phosphonoacetyl)-L-aspartate; Moore et al., 1982, Biochem. Pharmacol. 31, 3317-3321), A77 1726 (active metabolite of Leflunomide; Davis et al., 1996, Biochem. 35, 1270-1273) and Brequinar (Chen et al., 1992, Cancer Res. 52, 3251-3257). The presence of such inhibitors blocks the de novo synthesis of UMP, which is required for synthesizing RNA and DNA, thereby resulting in cell death. This cytotoxic effect can be circumvented by expressing the nucleotide sequence according to the invention encoding a polypeptide possessing UPRTase activity in the presence of uracil or by coexpressing this latter sequence with sequences encoding a polypeptide possessing CDase activity (where appropriate in fused form) in the presence of cytosine. As a consequence, only the transfected cells (cells which have incorporated the UPRTase/CDase sequences) will be able to grow in the presence of inhibitors of the pyrimidine synthesis pathway. Thus, the use according to the invention enables a transfected cell to be efficiently identified in, and/or isolated from, a cell mixture.

The present invention also relates to the use of the sequences or recombinant vectors according to the invention as negative selection markers For example, the sequences or recombinant vectors according to the invention can be used to select embryonic stem cells or cells obtained after nuclear transfer in which genes are interrupted or modified (e.g. in methods for preparing transgenic animals) (see, for example, Capecchi, 1989, Science 244, 1288-1292; Reid et al., 1990, Proc. Natl. Acad. Sci. USA 87, 4299-4303). Such a use, in combination with the gene for resistance to neomycin, for example, can make it possible to select the cells which have undergone an homologous recombination event and which will alone be able to grow in the presence of Geneticin and the corresponding fluorinated pyrimidines (5-FC when a nucleotide sequence encoding a CDase activity is used). The cells which have undergone a non-targeted recombination event are able to grow in the presence of Geneticin but not in the presence of the fluorinated pyrimidines. Another potential use as a negative selection marker is to be found in the plant field since, just like mammalian cells, plants do not possess any endogenous CDase activity. They can be sensitized to 5-FC by transfecting a nucleotide sequence according to the invention which enables an exogenous CDase to be expressed (see, for example, Perera et al. 1993, Plant. Mol. Biol. 23, 797-799).

The sequences or recombinant vectors according to the invention may also be used as negative selection marker for bacteria or yeast. In this particular embodiment yeast or bacteria lacking a native CDase gene are preferably used. Among those Bacteria, those disclosed in EP0792369BB1 are particularly preferred. For example, the sequence according to the invention may be used for cloning sequences, by homologous recombination, in a plasmid comprising the sequence according to the invention. In these experiments, the sequence according to the invention is located at the site where the sequence to be cloned has to be inserted. Therefore, after homologous recombination, cells comprising the desired plasmid are able to grow in the presence of 5-FC.

FIG. 1 shows the growth of LOVO tumor cells in CD1 nude mice treated with the vector according to the invention.

EXAMPLE 1

Construction of Fcu1-8

FCU1-8 has been constructed by directed mutagenesis of FCU1, starting from pCI-neoFCU1 (pTG13046) Arg in position 183 has been replaced by a Ser with a oligo 5'-gtattcttat-tactgatgatgg-3' (in order to modify A549en T) to give the plasmide pCI-neoFCU1-8 (pTG15546).

EXAMPLE 2

Expression of FCY1, FCU1 and Fcu1-8 in Mammalian Cells and Determination of the Activities CDase and UPRTase The stock of mammal COS7 transitorily transfected by the plasmides pCIneo (Promega), pCI-neoFCY1 (pTG15916), pCI-neoFCU1 (pTG13046) and pCI-neoFCU1-8 (pTG15546) was tested for CDase and UPRTase activities.

The protocol was as follows: 5 105 COS7 cells were sown with 37° C. 60 mm flasks containing 5 ml of DMEM/10% FCS medium. After 24 hours, the cells were treated by 20 µl of lipofectine (Gibco BRL) in absence or in the presence of 5 µg of plasmid. After 20 hours at 37° C. in 2 ml of medium DMEM, the cells were incubated in the presence of 5 ml of DMEM/10% FCS. After 48 hours, at 37° C., the cells were washed in PBS then suspended in 25 µl of lysis buffer (Tris-HCl pH 7.5 50 mM/NaCl 150 mM/EDTA 5 mM/DTT 1 mM/triton 1%). After 30 minutes of lysis at 4° C. followed by a centrifugation, the CDase and UPRTase activities was measured in the supernatant containing the cellular lysate.

For CDase activity: 4 µl of cellular lysate are incubated, 20 minutes at 37° C., in the presence of 2 µl of reactional CDase buffer (Tris-HCl pH 7.5 100 mM/[H3]5-FC 3 mM with 0.25 µCi/µl).

For UPRTase activity: 4 µl of cellular lysate are incubated, 20 minutes at 37° C. in the presence of 2 µl of reactional UPRTase buffer (Tris-HCl pH 7.5 100 mM/MgCl$_2$ 10 mM/5-PRPP 10 mM/[C14]5-FU 3 mM at 0.02 µCi/µl).

The enzymatic reactions are stopped at 100° C. during 1 minute. The aliquots of 1 µl are deposited on TLC polyethylenimine-cellulose plates (Merck). 5-FU is separated from the 5-FC by using a mixture water/butanol-1 (14%/86%) as solvent and the separation of 5-FUMP and 5-FU is carried out by using water as solvent. After migration, TLC plate was scanned in PosphorImager (445SI; Molecular Dynamics). The protein concentration was measured by the method of Bradford.

The results of the enzymatic activities, which are calculated from three independent measurements, are given in the following table:

|  | CDase pmoles of 5-FC transformed/min/mg of protein | UPRTase pmoles of 5-FU transformed/min/mg of protein |
| --- | --- | --- |
| not transfected | not detectable | not detectable |
| pCI-neo | not detectable | not detectable |
| pCI-neo FCY1 | 783 +/− 311 | not detectable |

-continued

|  | CDase pmoles of 5-FC transformed/min/mg of protein | UPRTase pmoles of 5-FU transformed/min/mg of protein |
|---|---|---|
| pCI-neo FCU1 | 9268 +/− 628 | 3866 +/− 518 |
| pCI-neo Fcu1-8 | 8263 +/− 782 | not detectable |

Compared to FCU1 gene, the Fcu1-8 mutant losses UPRTase activity with a conservation of CDase activity which is 10 times higher than CDase activity of native FCY1 gene. The Arg183 change in Ser in gene FCU1 leads to a loss in UPRTase activity without modifying CDase activity.

EXAMPLE 3

Construction of an Adenovirus Expressing FCU1 (AdTG14800)

The XhoI-MluI fragment of pCI-neoFCU1 (pTG13046) containing FCU1 gene is isolated and introduced into the transfer vector pTG13387 cleaved by these same enzymes, to give the transfer vector pTG14799. The adenoviral vector AD-FCU1 (pTG14800) is reconstituted by homologous recombination in the BJ 5183 E. coli between the fragment PacI-BstEII of pTG14799 and the vector pTG6624 linearized by ClaI. Final construction AD-FCU1 contains the E1 and E3 deleted Ad5 genome (nucleotides 459 to 3510 and 28249 to 30758) and instead of E1, an expression cassette comprising FCU1 gene is placed under the control of the CMV promoter and β-globine/IgG and followed and the poly A sequences of bGH. The adenoviral particles expressing FCU1 (AdTG14800) are generated by transfection in a complementation cell line (for example line PERC6).

EXAMPLE 4

Construction of an Adenovirus Expressing Fcu1-8 (AdTG15606)

The XhoI-MluI fragment of pCI-neoFCU1-8 (pTG15546) containing the Fcu1-8 gene is isolated and introduced into the transfer vector pTG13387 cleaved by these same enzymes, to give the transfer vector of pTG15547. The adenoviral vector AD-FCU1-8 (pTG15606) is reconstituted by homologous recombination in the BJ 5183 E. coli strain between the fragment PacI-BstEII of pTG15547 and the vector pTG6624 linearized by ClaI. Final construction AD-FCU1-8 contains the Ad5 genome deleted of the E1 (NT 459 to 3510) and E3 (NT 28249 to 30758) regions and instead of E1, a expression cassette comprising the Fcu1-8 gene placed under the control of the CMV early promoter hybrid β-globine/IgG and MVC and the followed by poly A sequences of bGH. The adenoviral particles expressing Fcu1-8 (AdTG15606) are generated by transfection in a cell line complementating the E1 function, for example PERC6.

EXAMPLE 5

Infection by the Adenovirus Expressing FCU1 (AdTG14800) and Fcu1-8 (AdTG15606)

In Vitro Results
Determination of the Activities CDase and UPRTase
The human tumoral cell line A549 (ATCC Col-185) was infected by an empty adenovirus (AdTG15149), an adenovirus expressing FCU1 (AdTG14800) and by an adenovirus expressing Fcu1-8 (AdTG15606). The infection protocol was as follows: 5 106 cells in suspension in 50 µl of PBS-2% FCS-cations 1% are incubated 30 minutes at 37° C. in the presence of the adenovirus at MOI 5. The totality of the 5 106 cells is then incubated in 60 mm flasks in the presence of 5 ml of DMEM-10% FCS. After 24 hours at 37° C., the cells were washed in PBS then resuspended in 25 µl of lysis buffer (Tris-HCl pH 7.5 50 mM/NaCl 150 mM/EDTA 5 mM/DTT 1 mM/triton 1%). After 30 minutes of lysis at 4° C. followed by a centrifugation, the CDase and UPRTase activities was measured in the supernatant containing the cellular lysate (according to the previously described protocol).

The results of the enzymatic activities, which are calculated from three independent measurements, are given in the following table:

|  | CDase pmoles of 5-FC transformed/min/mg of protein | UPRTase pmoles of 5-fu transformed/min/mg of protein |
|---|---|---|
| not infected | not detectable | not detectable |
| Ad-empty (AdTG15149) | not detectable | not detectable |
| Ad-FCU1 (AdTG14800) | 12000 +/− 1870 | 1110 +/− 190 |
| Ad-FCU1-8 (AdTG15606) | 12970 +/− 1350 | not detectable |

For the cells infected by an adenovirus expressing Fcu1-8, the results indicate a loss of UPRTase activity whereas CDase activity is preserved.

EXAMPLE 6

Construction of MVA Expressing FCU1 (MVATG15637)

The transfer vector Mva-fcu1 (pTG15637) is reconstituted by homologous recombination in the BJ 5183 E. coli strain between the HindIII-KpnI fragment of pCI-neoFCU1 (pTG13046) and the vector pTG14269 linearized by XhoI. This transfer vector MVA-fcu1 (pTG15637) contains the expression cassette of the FCU1 gene placed under the control of the p11K7.5 promoter and framed by the sequences bordering deletion III of MVA. MVA Particles expressing FCU1 (MVATG15637 with FCU1 inserted in deletion III and under the control of the p11K7.5 promoter) are generated by homologous recombination between the MVAN33 and the plasmid pTG15637 in the embryonic chicken cells.

EXAMPLE 7

Construction of Mva Expressing Fcu1-8 (MVATG15638)

The transfer vector MVA-FCU1-8 (pTG15638) is reconstituted by homologous recombination in the BJ 5183 E. coli strain between the HindIII-KpnI fragment of pCI-neoFCU1-8 (pTG15546) and the vector pTG14269 linearized by XhoI. This transfer vector MVA-FCU1-8 (pTG15638) contains the expression cassette of the Fcu1-8 gene placed under the control of the p11K7.5 promoter and framed by the sequences bordering deletion III of MVA. MVA particles expressing Fcu1-8 (MVATG15638 with Fcu1-8 inserted in deletion III and under the control of the p11K7.5 promoter) are generated by homologous recombination between the MVAN33 and the plasmid pTG15638 in embryonic chicken cells.

EXAMPLE 8

Infection by MVA Expressing FCU1 (MVATG15637) and FCU1-8 (MVATG15638)

In Vitro Results

Determination of the Activities CDase and UPRTase

The human tumoral cell line A549 (ATCC CCCL-185) was infected by an empty MVA (MVAN33), MVA expressing FCU1 (MVA15637) and of MVA expressing FCU1-8 (MVA15638). The infection protocol was as follows: 5 106 cells in suspension in 50 µl of PBS-FCS 2%-cations 1% are incubated 30 minutes at 37° C. in the presence of the adenovirus at an MOI 0.05. The totality of the 5 106 cells is then incubated in a 60 mm flasks in the presence of 5 ml of DMEM-10% FCS. After 24 hours at 37° C., the cells were washed in PBS then resuspended in 25 µl of lysis buffer (TRIS-HCl pH 7.5 50 mM/NaCl 150 mM/EDTA 5 mM/DTT 1 mM/triton 1%). After 30 minutes of lysis at 4° C. followed by a centrifugation, the CDase and UPRTase activities was measured in the supernatant containing the cellular lysate (according to the previously described protocol).

The results of the enzymatic activities, which are calculated from three independent measurements, are given in the following table:

|  | CDase pmoles of 5-FC transformed/min/mg of protein | UPRTase pmoles of 5-FU transformed/min/mg of protein |
|---|---|---|
| not infected | not detectable | not detectable |
| MVA-empty (MVAN33) | not detectable | not detectable |
| MVA-FCU1 (MVATG15637) | 177860 +/− 6650 | 43860 +/− 4230 |
| MVAV-FCU1-8 (MVATG15638) | 232220 +/− 15580 | not detectable |

For the cells infected by MVA expressing FCU1-8, the results indicate a loss of UPRTase activity whereas CDase activity is preserved.

EXAMPLE 9

Experiment In Vivo 5.106 human cells LoVo (adenocarcinoma of colon) are injected by intracutaneous way in 8 groups of 15 CD1 nude mouse at J0. As soon as the tumours have a volume of 30-50 mm3 (J+10), MVA are injected by intratumoral administration with an amount of 5·10$^6$ PFU. From J+10, 0.5 ml water or 0.5 ml of a 0.5% 5-FC solution are given per os, twice by day and during 14 days. Volumes of the tumours (FIG. 1) highlight a better control of the size of the tumours with group MVA-fCU1-8/5-FC compared to group MVA-FCU1/5-FC.

What is claimed:

1. A recombinant polypeptide comprising the amino acid sequence of SEQ ID NO:1, wherein said polypeptide has cytosine deaminase (CDase) activity but no uracil phosphoribosyltransferase (UPRTase) activity and no thymidine kinase activity.

2. The recombinant polypeptide according to claim 1, consisting of the amino acid sequence of SEQ ID NO:1.

3. A composition which comprises a polypeptide according to claim 1 in combination with a pharmaceutically acceptable excipient.

4. The recombinant polypeptide according to claim 1, characterized in that it retains CDase activity and loses UPRTase activity relative to a recombinant polypeptide comprising the amino acid sequence of SEQ ID NO:1 in which the Ser residue in position 183 is substituted with an Arg residue.

* * * * *